(12) United States Patent
Steffens et al.

(10) Patent No.: US 9,932,299 B2
(45) Date of Patent: Apr. 3, 2018

(54) PROCESS FOR SEPARATING AN ISOCYANATE PREPARED BY PHOSGENATION OF A PRIMARY AMINE IN THE GAS PHASE FROM THE GASEOUS CRUDE PRODUCT OF THE PHOSGENATION

(71) Applicant: Bayer MaterialScience AG, Leverkusen (DE)

(72) Inventors: Friedhelm Steffens, Leverkusen (DE); Bastian Mahr, Bergisch Gladbach (DE)

(73) Assignee: Covestro Deutschland AG, Leverkusen (DE)

( * ) Notice: Subject to any disclaimer, the term of this patent is extended or adjusted under 35 U.S.C. 154(b) by 237 days.

(21) Appl. No.: 14/765,870

(22) PCT Filed: Feb. 5, 2014

(86) PCT No.: PCT/EP2014/052260
§ 371 (c)(1),
(2) Date: Aug. 5, 2015

(87) PCT Pub. No.: WO2014/122180
PCT Pub. Date: Aug. 14, 2014

(65) Prior Publication Data
US 2015/0368190 A1 Dec. 24, 2015

(30) Foreign Application Priority Data
Feb. 8, 2013 (EP) ..................... 13154596

(51) Int. Cl.
*C07C 263/20* (2006.01)
*C07C 263/18* (2006.01)
(Continued)

(52) U.S. Cl.
CPC ............ *C07C 263/20* (2013.01); *B01D 3/009* (2013.01); *C07C 263/18* (2013.01); *C07C 253/00* (2013.01)

(58) Field of Classification Search
CPC .............................. C07C 263/20; B01D 3/009
See application file for complete search history.

(56) References Cited

U.S. PATENT DOCUMENTS 4,101,590 A * 7/1978 Sato ........................ C07C 37/72
568/750
4,195,031 A * 3/1980 Reichmann ........... C07C 263/04
560/345
(Continued)

FOREIGN PATENT DOCUMENTS

| EP | 1935875 A1 * | 6/2008 | ........... C07C 263/10 |
| EP | 2463273 A1 | 6/2012 | |
| WO | WO 2007028715 A1 * | 3/2007 | ............ B01F 5/0453 |

*Primary Examiner* — In Suk C Bullock
*Assistant Examiner* — Youngsul Jeong
(74) *Attorney, Agent, or Firm* — Donald R. Palladino

(57) ABSTRACT

The present invention relates to a process for separating an isocyanate prepared by reaction of a primary amine with an excess of phosgene in the gas phase from the gaseous crude product obtained in the reaction, wherein
(i) the gaseous crude product is partially liquefied by contacting with a quenching liquid,
(ii) the gas phase obtained in step (i) is partially condensed,
(iii) the condensate obtained in step (ii) is used as the quenching liquid in step (i),
(iv) the portions of the gas phase that were not condensed in step (ii) are at least partially liquefied,
(v) the liquid phase obtained in step (iv) is likewise used as the quenching liquid in step (i), and
(vi) the liquid phase obtained in step (i) is worked up to the pure isocyanate without previously being used as quenching liquid.

14 Claims, 1 Drawing Sheet

(51) Int. Cl.
*B01D 3/00* (2006.01)
*C07C 253/00* (2006.01)

(56) References Cited

U.S. PATENT DOCUMENTS

| | | |
|---|---|---|
| 4,847,408 A | 7/1989 | Frosch et al. |
| 5,633,396 A | 5/1997 | Bischof et al. |
| 6,800,781 B2 | 10/2004 | Herold et al. |
| 6,808,747 B1 | 10/2004 | Shih et al. |
| 7,084,297 B2 | 8/2006 | Woelfert et al. |
| 7,488,842 B2 | 2/2009 | Knoesche et al. |
| 7,541,487 B2 | 6/2009 | Pohl et al. |
| 7,615,662 B2 * | 11/2009 | Pohl .................. C07C 263/10 560/347 |
| 7,915,444 B2 | 3/2011 | Woelfert et al. |
| 8,563,768 B2 | 10/2013 | Bruns et al. |
| 8,759,568 B2 | 6/2014 | Lehr et al. |
| 8,809,575 B2 | 8/2014 | Knoesche et al. |
| 9,024,057 B2 | 5/2015 | Biskup et al. |
| 2003/0233013 A1 * | 12/2003 | Lokum ............. C07C 263/20 560/352 |
| 2009/0054684 A1 * | 2/2009 | Stutz .................. C07C 263/10 560/347 |
| 2011/0257428 A1 * | 10/2011 | Knoesche .......... C07C 263/10 560/347 |
| 2011/0306789 A1 | 12/2011 | Carvin et al. |
| 2012/0123152 A1 * | 5/2012 | Bruns ................. C01B 31/28 560/347 |

* cited by examiner

PROCESS FOR SEPARATING AN ISOCYANATE PREPARED BY PHOSGENATION OF A PRIMARY AMINE IN THE GAS PHASE FROM THE GASEOUS CRUDE PRODUCT OF THE PHOSGENATION

CROSS-REFERENCE TO RELATED APPLICATION

This application is a National Phase application to PCT/EP2014/052260, filed Feb. 5, 2014 and European Application No.: 13154596.4, filed Feb. 8, 2013.

FIELD

The present invention relates to a process for separating an isocyanate prepared by reaction of a primary amine with an excess of phosgene in the gas phase from the gaseous crude product obtained in the reaction, wherein
(i) the gaseous crude product is partially liquefied by contacting with a quenching liquid,
(ii) the gas phase obtained in step (i) is partially condensed,
(iii) the condensate obtained in step (ii) is used as the quenching liquid in step (i),
(iv) the portions of the gas phase that were not condensed in step (ii) are at least partially liquefied,
(v) the liquid phase obtained in step (iv) is likewise used as the quenching liquid in step (i), and
(vi) the liquid phase obtained in step (i) is worked up to the pure isocyanate without previously being used as quenching liquid.

BACKGROUND

The preparation of isocyanates, in particular diisocyanates, in the gas phase has been described in the prior art for a relatively long time and is used industrially, in particular for the production of toluylene diisocyanate, 1,6-hexamethylene diisocyanate, isophorone diisocyanate and diisocyanato-dicyclohexylmethane. In all processes there is formed a gaseous crude product which comprises at least isocyanate, hydrogen chloride and unreacted phosgene (phosgene is always used in excess) and which must be worked up further in order to obtain the desired isocyanate in pure form.

Such a process is described, for example, in EP 0 289 840 B1. The diisocyanates formed in a tubular reactor are not thermally stable at the reaction temperatures of up to 500° C. Rapid cooling of the reaction gases after the phosgenation reaction to temperatures below 150° C. is therefore necessary in order to avoid the formation of undesirable secondary products by the thermal decomposition of diisocyanate or by a further reaction. In EP 0 289 840 B1 or EP 0 749 958 B1, the gaseous mixture continuously leaving the reaction chamber, which comprises inter alia diisocyanate, phosgene and hydrogen chloride, is to that end passed into an inert solvent, for example dichlorobenzene. A disadvantage of this process is that the flow speed with which the gas mixture is passed through the solvent bath must be chosen to be relatively low because solvent and the compounds dissolved therein would be entrained if the speed were too high. The liquid compounds would have to be separated from the gas in a subsequent step. A further disadvantage is that, owing to the low flow speed and a low heat transfer, large solvent containers must be used in order to achieve cooling.

Also known are processes which use heat exchangers for cooling the reaction gases and/or relax the gases in vacuo (DE 101 58 160 A1). The disadvantage of heat exchangers is that, because of the poor heat transfer, large exchange surfaces, and thus large heat exchangers, are required for effective cooling. In addition, deposits of solids on the comparatively cold surfaces of the heat exchangers can occur owing to secondary reactions of the gas mixture, such as, for example, decomposition, polymerisation or precipitation.

In the process according to EP 1 761 483 B1, it is attempted to shorten the dwell time between the end of the reaction and the cooling zone by providing a region of reduced flow cross-section between the reaction zone and the zone in which termination of the reaction is effected.

Application WO2007/014936 A2, method for producing isocyanates (in the gas phase), describes a quenching zone in which the gaseous crude product is cooled rapidly by injection of a quenching liquid. In the quenching zone, the reaction mixture, which consists substantially of the isocyanates, phosgene and hydrogen chloride, is mixed intensively with the injected liquid. Mixing is carried out in such a manner that the temperature of the reaction mixture, starting from 200 to 570° C., is lowered to 100 to 200° C. and the isocyanate comprised in the reaction mixture is transferred wholly or partially into the injected liquid droplets by condensation, while the phosgene and the hydrogen chloride remain substantially wholly in the gas phase. Solvents, isocyanate mixtures and solvent/isocyanate mixtures are mentioned as possible quenching liquids. Mention is made of the injection of a quenching liquid to cool the reaction mixture and selectively dissolve the diisocyanate that has formed in the solvent, a first separation into a liquid phase and gas phase comprising predominantly phosgene and hydrogen chloride as constituents being carried out. The two phases are subsequently fed to a corresponding working up. Possible ways of optimising this method step are not discussed.

WO 2011/003532 A1 also discloses a method for rapidly cooling the gaseous reaction mixture by injecting a quenching liquid into the gas mixture flowing continuously from the reaction zone into the downstream quenching zone.

The injection of quenching liquid by means of at least two spray nozzles, which are arranged at the entry to the quenching zone, is disclosed in EP 1 403 248 B1. Suitable quenching liquids here are organic solvents or a mixture of different organic solvents which do not react with the diisocyanate that has formed. A solution of the diisocyanate that has formed in a suitable organic solvent can also be used, which reduces the amount of solvent used. The diameter of the quenching zone can be larger or smaller than the diameter of the reaction zone. Quenching of the reaction gases can take place in one stage or in a plurality of stages.

This system is optimised according to the teaching of EP 1 935 875 B1 in that, in order to terminate the reaction, the reaction mixture is guided from the reaction chamber through a cooling stretch into which liquids are injected in two zones, so that direct cooling in the cooling stretch takes place in one stage (i.e. yielding only one condensation mixture) in two or more cooling zones connected one behind the other. At least in the second zone, a cooling liquid is used that comprises the prepared isocyanate in considerable amounts (see patent claim 1, last paragraph). The diisocyanate produced is thereby obtained in a common condensation mixture. This mixture is preferably collected in a liquid collecting vessel arranged beneath the cooling stretch. This condensation mixture can be discharged in order to separate off the isocyanate that has been produced or, preferably after cooling has taken place, can partially be fed back to one or more cooling zones of the cooling stretch. A possible disadvantage of the use of the liquid crude product mixture from the gas-phase phosgenation is the occurrence of contamination of the described cooler before entry into the quencher. Causes of this can be undesirable secondary products or polymer compounds from the phosgenation reaction. In addition to the condensation mixture in the collecting vessel, there is obtained downstream of the cooling stretch a gas stream comprising at least hydrogen chloride, phosgene, optionally solvent, and the isocyanate that has been produced. This gas stream is removed from the collecting vessel and fed to a washing column, where it is largely freed of its isocyanate components. This washing preferably takes place counter-currently with solvent. The wash phase so obtained, consisting of diisocyanate and predominantly solvent, is used in a preferred embodiment as the quenching liquid of the first cooling zone of the cooling stretch. The residual gas from the washing column consists substantially of phosgene, hydrogen chloride and solvent. These vapours leave the column at the top, whereby, in a preferred embodiment, by means of partial condensation, the solvent component is largely retained by way of two condensers having different coolant temperatures and is fed back to the column as partial condensate. The residual gas obtained thereafter, which consists substantially of phosgene, hydrogen chloride and solvent residues, is then treated further in a manner known per se, as described, for example, in EP 1 849 767 B1.

The use of different suitable quenching liquid streams is likewise mentioned in EP 1 935 876 A1. Reference is also made thereby to the use as quenching liquid of the washing liquid from the gas washing of the vapours leaving the condensate collecting vessel after the quencher.

EP 2 196 455 A1 also refers to a plurality of cooling zones in the quenching stage. Mention is made here for the first time of the integrated combination of the cooling zones of a plurality of reactors with a quenching stage.

WO 2010/063665 A1 makes reference to a possible problem of the quenching variants known hitherto. If at least a portion of the quenching liquid is removed from the collecting vessel after the quencher, that is to say the liquid crude product, there is the possibility that solids may be present, which can block the quenching nozzles. Various techniques, such as, for example, centrifugation, removal by distillation of the liquid component provided for the quenching, or filtration, are described. In order to adjust the temperature of the chosen quenching stream for the problem posed, the stream can be cooled, or heated, by means of a heat exchanger. This specification discloses (p. 12, l. 6 to 9, p. 13, second paragraph) various sources for the quenching medium: a part-stream 15 branched from the phase separator 9 provided downstream of the quencher 3 (which necessarily also comprises isocyanate liquefied in the quencher), fresh solvent 19, a portion of the liquid phase 13 obtained in the phase separator, and a part-stream of the two-phase product stream 7. The specification does not disclose an embodiment in which the quenching medium is obtained from the gas phase 11 obtained in the phase separator 9 and recycling of isocyanate liquefied in the quencher is dispensed with completely.

In WO 2010/115908 A2, a specific form of the quencher is disclosed. In order to prevent subsequent reactions of the reaction gas at or downstream of the quenching stage, the quenching nozzles and the arrangement thereof are so designed that largely complete wetting of the wall in the quenching region takes place. The entire reaction mixture is thereby included. There are proposed as quenching liquids solvents as well as mixtures with isocyanate or crude mixture from the phosgenation reaction, optionally after particle removal.

EP 2 463 273 A1 discloses a process variant for isocyanate concentrations of greater than 70% by mass in the liquid bottom product leaving the quenching zone. The stream leaving the quenching zone in gas form is passed directly into a jacket-cooled condenser, without passing through a washing column. The gas stream that remains is fed directly to phosgene recovery. Despite the high temperature and high isocyanate concentration in the liquid bottom product of the quenching zone, no information is given regarding residual isocyanate contents in the gas stream that remains. The condensate stream is combined with the condensate of the vapour stream formed by relaxation of the liquid bottom product from the quenching zone, and is fed back as quenching liquid.

The specifications hitherto were concerned, in the quencher region of the gas-phase phosgenation of diamines, substantially with optimising the actual quencher systems. Apart from a few exceptions, the peripheral systems associated with the quencher were disregarded. The exceptions are, for example, as mentioned above, the use of condensation mixture from the liquid collecting vessel of the quencher or of the condensate of the vapour stream formed by flash vaporisation of the condensation mixture, or the use as the quenching liquid of the washing liquid from the gas washing of the vapours leaving the condensate collecting vessel after the quencher. By using condensation mixture from the liquid collecting vessel of the quencher, the amount of solvent required for cooling the reaction gas is reduced by replacing externally supplied quenching liquid by diisocyanate produced in the gas-phase phosgenation and solvent already comprised in the condensate. Likewise, the total amount of quenching liquid can be reduced by using some of the washing liquid from the gas washing of the vapours leaving the condensate collecting vessel after the quencher. Both procedures lead to a reduction of the solvent circulating in the process as a whole and accordingly, when used successfully, contribute towards reducing the energy consumption and can optionally contribute towards reducing costs in terms of apparatus.

A typical process of the prior art will be explained by way of example by means of the first figure (FIG. 1):

The gaseous crude product (101), consisting predominantly of isocyanate, hydrogen chloride and phosgene used in a superstoichiometric amount, is cooled quickly in the quencher (A11) by injection of quenching liquid (105 and 116) in order to avoid undesirable subsequent reactions. The stream (102) that leaves the quencher in the liquid state and comprises especially isocyanate and quenching liquid is passed for the smaller part to product purification and for the larger part via the quench cooler (W11) to the quencher as quenching liquid. Owing to the large circulating stream, a pump (P11) of an appropriately large size must be installed, and thermal stress of the product by repeated contacting with the hot gas stream from the reaction must be taken into account, which leads to losses of yield and an increased outlay in terms of working up. Solids and high boilers formed in or introduced into the reaction or quenching zone pass with the liquid quench product into the quench cooler (W11) and the quenching nozzles and can cause contamination there.

The substance stream (106) that leaves the quencher in gas form and comprises especially vaporised quenching liquid, hydrogen chloride and phosgene is passed to the washing column (A12), in order to remove residual contents of isocyanate from the vapour stream as completely as possible. The higher the content of isocyanates in the substance stream (106) that is supplied, the greater the washing liquid stream (solvent) required at the top of the washing column, and the greater the number of separator stages required for reliable retention. The washing liquid stream is composed of the condensate (113) of the condenser (W12) and additional solvent (110), which may comprise low boilers such as phosgene but is virtually isocyanate-free. The virtually isocyanate-free vapour stream (114) comprises especially phosgene and hydrogen chloride. The liquid bottom run-off (115) comprises especially solvent and is advantageously fed to the quencher as quenching liquid.

The temperature of the substance streams at the outlet of the quenching step must be adjusted while balancing contrary aims, inter alia, on the one hand, between low thermal product stress and low solvent and isocyanate content in the vapour stream to be purified and recycled (low temperature is positive) and, on the other hand, low carbamic acid chloride formation and low energy requirement in the product working-up (high temperature is positive). The temperature of the substance streams at the outlet of the quenching zone is determined, with a given gas stream from the reaction zone, by the amount, temperature and composition of the quenching liquid streams.

On the basis of this prior art, there was a need for a further optimisation of the quenching of a gaseous isocyanate crude product. In particular, the process sections of (a) transfer of the liquid crude product mixture from the quencher into the further working-up stages, (b) treatment of the gas phase (vapours) obtained in the quencher, including gas washing, and (c) supply of the quenching stage against the background of low operating and apparatus costs with high availability and simple, reliable controllability were to be optimised further.

SUMMARY

Taking account of this need, the present invention provides a process for separating an isocyanate prepared by reaction of a primary amine with an excess
(i) the gaseous crude product (201), which comprises at least isocyanate, hydrogen chloride and unreacted phosgene, is converted by contacting with, preferably by injection of, at least one quenching liquid into a liquid phase (202) comprising at least quenching liquid and isocyanate and at least one gas phase (206) comprising at least hydrogen chloride and phosgene (so-called "quenching" of the gaseous crude product),
(ii) the gas phase (206) obtained in step (i) is partially condensed,
(iii) the condensate (208) obtained in step (ii) is used as the quenching liquid in step (i),
(iv) the portions (207) of the gas phase (206) that were not condensed in step (ii) are at least partially liquefied to give a liquid phase (215),
(v) the liquid phase (215) obtained in step (iv) is likewise used as the quenching liquid in step (i), and
(vi) the liquid phase (202) obtained in step (i) is worked up to the pure isocyanate without previously being used as quenching liquid.

DETAILED DESCRIPTION

Figure 1:
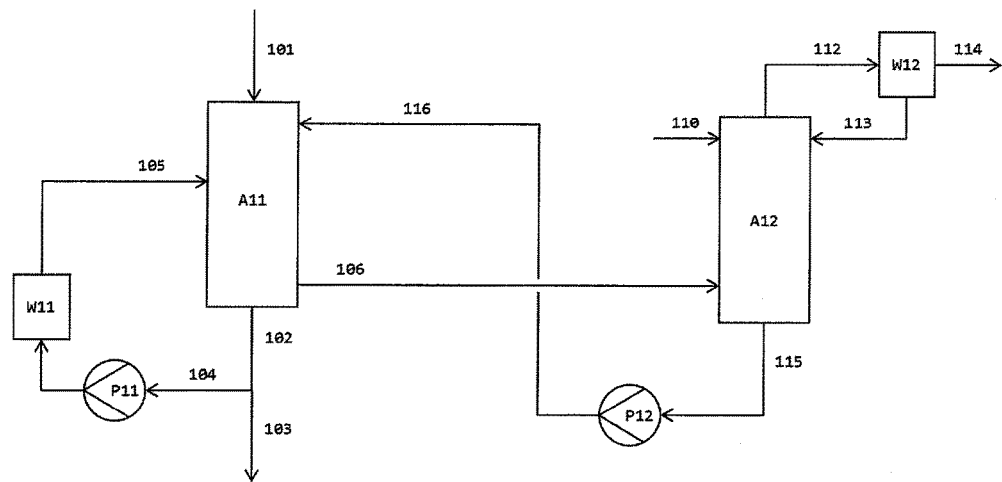
FIG. 1 is a schematic illustration of a typical process for separating an isocyanate prepared by reaction of a primary amine with an excess of phosgene in the gas phase from the gaseous crude product of the prior art.

Within the context of the present invention, the word "a" in connection with countable items is to be understood as being a numeral only when this is stated expressly (e.g. by the expression "exactly one"). If, for example, "a condenser" is mentioned in the following, the word "a" is to be interpreted merely as an indefinite article and not as a numeral; accordingly, this also includes an embodiment in which two or more condensers are connected in series.

The limitation "without previously being used as quenching liquid" in step (vi) of the process according to the invention means that isocyanate liquefied in step (i) is not a constituent of the quenching liquid(s) used in step (i), that is to say, unlike in the prior art, there is no partial recycling of the liquefied isocyanate into the "quenching" of the gaseous crude product (201).

Embodiments of the process according to the invention are described in greater detail below. Different embodiments can be combined with one another as desired, unless the contrary is clearly apparent to the person skilled in the art from the context. Reference numerals with a "2" as the first digit refer to the second figure (FIG. 2), in which a preferred form of the process according to the invention is shown schematically.

The reaction of a primary amine with an excess of phosgene in the gas phase in order to obtain the gaseous crude product (201) comprising the corresponding isocyanate can in principle be carried out according to any process of gas-phase phosgenation known from the prior art. Examples of suitable gas-phase phosgenation processes are described in EP 0 570 799 A1, EP 1 555 258 A1, EP 1 526 129 A1 and DE 101 61 384 A1, as well as in particular for aliphatic isocyanates in EP 0 289 840 B1 and EP 1 754 698 B1.

Suitable primary amines are in particular the isomers of toluylenediamine (TDA hereinbelow), the isomers of diphenylmethanediamine (MDA hereinbelow), 1,6-hexamethylenediamine (HDA hereinbelow), the isomers of isophoronediamine (IPDA hereinbelow) and the isomers of diaminodicyclohexylmethane (H12-MDA hereinbelow). TDA is particularly preferred, the precise isomer composition not being important for the process according to the invention. TDA which is preferably used conventionally comprises from 78% by mass to 82% by mass 2,4-TDA and from 18% by mass to 22% by mass 2,6-TDA, based on the total mass of the 2,4- and 2,6-TDA isomers. Based on the total mass of the TDA, the 2,4- and 2,6-TDA isomers preferably account in total for from 95.0% by mass to 100% by mass, particularly preferably from 98.0% by mass to 100% by mass.

The primary amine is reacted with phosgene. Both continuous and batchwise operation are possible. Phosgenation with continuous operation is preferred. The reaction preferably takes place at a temperature of from 200° C. to 600° C., preferably from 300° C. to 500° C., and an absolute pressure of from 150 mbar to 10 bar, preferably from 1.0 bar to 3.0 bar. The molar excess of phosgene is preferably from 20% to 400% of theory.

Step (i) of the process according to the invention, the rapid cooling and partial liquefaction ("quenching") of the gaseous crude product (201) of the phosgenation by contacting with, preferably by injection of, a quenching liquid, can take place in any desired apparatus (A21) known from the prior art. Suitable forms are described, for example, in EP 1 403 248 A1, see in particular the drawings with the associated explanations in paragraphs [0017] to [0019], and EP 1 935 875 A1, see in particular paragraphs [0015] to [0022] and [0033] to [0045], but it must be ensured within the context of the present invention that isocyanate from stream 202 liquefied in step (i) is not a constituent of the quenching liquid (see step (vi) of the present invention).

In addition to the quenching liquids from step (iii) and step (v) (see below for further details), a fresh stream of an organic solvent can additionally be used as the quenching liquid (not shown in FIG. 2). Preferred solvents are chlorinated aromatic hydrocarbons, such as, for example, chlorobenzene, o-dichlorobenzene, p-dichlorobenzene, trichlorobenzenes, the corresponding chlorotoluenes or chloroxylenes, chloroethylbenzene, monochlorodiphenyl, α- and β-naphthyl chloride, benzoic acid ethyl ester, phthalic acid dialkyl esters, diisodiethyl phthalate, toluene and xylenes. Particularly preferred solvents are chlorobenzene and the isomers of dichlorobenzene, with o-dichlorobenzene being extraordinarily particularly preferred. This additional stream of fresh organic solvent preferably has a temperature of from 40° C. to 150° C. However, even only partial recycling of the liquid phase 202 as quenching liquid is excluded according to the invention (see step (vi) of the present invention). This has the effect that the quenching liquid(s) used comprise at most insignificant amounts of isocyanate (from small amounts of isocyanate not liquefied in step (i), which leave the quencher A21 with the gas stream 206).

In this manner there are obtained in step (i) a liquid phase (202) comprising at least quenching liquid and isocyanate and a gas phase (206) comprising at least hydrogen chloride and phosgene.

Step (ii) of the process according to the invention, the partial condensation of the gas phase (206) obtained in step (i), can be carried out in any desired condenser (W23) known from the prior art. The condenser (W23) can be in multi-stage form, for example in order to use various cooling media and/or in order to obtain a plurality of process condensate qualities, which can optionally be fed back in at different points in the process. The condenser (W23) is preferably in the form of an indirect cooler with trickling liquid. A possible form is, for example, a trickle-film condenser in which a portion of the condensate is fed back to the same condenser as trickling liquid. As well as comprising hydrogen chloride and phosgene, the gas phase (206) generally also comprises residual amounts of isocyanate and quenching liquid, because the separation thereof from phosgene and hydrogen chloride in step (i) generally does not take place completely. In the condenser used in step (ii), the majority of the quenching liquid that remained in the gas phase (206) and of the isocyanate is condensed. This is effected by cooling the gas phase (206), which is preferably passed into the condenser with a temperature of from 120° C. to 250° C., to a temperature of preferably from 40° C. to 170° C. Step (ii) is preferably used to obtain steam, preferably low-pressure steam at 6 bar.

The condensate (208) obtained comprises especially solvent (from the quenching liquid) and is therefore particularly suitable for recycling as quenching liquid (209). Because it is the condensate from a stream in vapour form, the proportion of high boilers and the risk of solids contents is very much lower than in the liquid crude product mixture (202). The tendency for contamination in the heat exchanger (W23), pump (P23), the quenching nozzles for stream (209) and associated piping is thus substantially lower than a possible tendency for contamination in the comparable plant parts carrying liquid crude product mixture in the prior art (pump P11, heat exchanger W11, quenching nozzles for stream 105, associated piping).

In addition to the gas phase (206) obtained in step (i),
(a) a portion (219) of the condensate (208) obtained in step (ii) or
(b) a solvent stream (220) or
(c) stream (a) (219) and stream (b) (220)
can also be passed into the condenser (W23). The condensation of the vapours (206) is thereby facilitated, heat transfer surfaces are wetted uniformly, adhesions are avoided or rinsed off, and/or an absorption action is achieved.

The condenser (W23) is operated on the process side preferably co-currently with vapour and liquid phase, in order to permit high vapour speeds and small apparatus dimensions. However, it can also be configured counter-currently, in particular in order to achieve more than one theoretical separator stage, in order to minimise the proportion of isocyanate in the emerging vapour stream (207).

The condensate (208) obtained in step (ii) is removed from the condenser, if required conveyed by means of a pump (P23), and used in step (iii) as the quenching liquid (209) in the quenching stage (step (i)). With a suitable apparatus set-up (free liquid run-off is ensured), the pump can be omitted. If required, the stream (208) can be cooled further by means of an additional cooling medium before it is used as quenching liquid (209). The quenching liquid (209) is brought into contact with, preferably injected into, the gaseous product stream (201) preferably at a temperature of from 30° C. to 170° C. The use of the condensate (208) as the quenching liquid replaces the quenching liquid (105) from the prior art. In other words, it is not necessary in the process according to the invention to use considerable portions of the crude product liquefied in the quenching zone (A21) as the quenching liquid. The associated disadvantages of the prior art, which have been described above, are therefore avoided. In particular, the quench cooler (W11), with a potential tendency for contamination, and the associated circulating pump (P11) are unnecessary. By completely dispensing with recycling into the quencher of the crude product mixture liquefied in the quenching zone (A21) or of the condensate of the vapour (with a significant isocyanate content) formed by flash vaporisation of the liquid crude product mixture, the tendency to form deposit build-ups in pipelines and in the quench zone itself, and also product decomposition, are reduced.

Step (iv) of the process according to the invention, the at least partial liquefaction of the portions (207) of the gas phase (206) that were not condensed in step (ii), is preferably carried out in a washing column (A22) with at least one separator stage, at least one solvent stream being fed to the washing column (A22) as washing liquid. Particularly preferably, the gaseous top stream (212) of the washing column (A22) is condensed in a condenser (W22), and the condensate (213) so obtained is fed back into the washing column (A22) as additional washing liquid. Suitable washing columns (A22) for step (iv) are described, for example, in Perry's Chemical Engineers' Handbook, 7th Edition, McGraw-Hill, Chapter 14, "Gas Absorption and Gas-Liquid System Design". Preferred solvents for step (iv) are chlorinated aromatic hydrocarbons, such as, for example, chlorobenzene, o-dichlorobenzene, p-dichlorobenzene, trichlorobenzenes, the corresponding chlorotoluenes or chloroxylenes, chloroethylbenzene, monochlorodiphenyl, α- and β-naphthyl chloride, benzoic acid ethyl ester, phthalic acid dialkyl esters, diisodiethyl phthalate, toluene and xylenes. Particularly preferred solvents are chlorobenzene and the isomers of dichlorobenzene, with o-dichlorobenzene being extraordinarily particularly preferred. The at least one solvent stream can consist of fresh solvent. It is, however, also possible to use recycled solvent-comprising streams in the process.

In an embodiment, exactly one solvent stream (different from (213)) is fed to the washing column (A22).

In a further embodiment, a solvent stream (210) is fed to the washing column (A22) above the separator stage, where a plurality of separator stages are present above the uppermost separator stage. If a recycled solvent-comprising stream is to be used as the solvent stream (210) instead of fresh solvent, it must be ensured that it comprises the isocyanate that is to be separated off in an amount by mass of not more than 100 ppm, based on the total mass of the solvent stream (210), in order to avoid the formation of decomposition products.

Alternatively to or in combination with this embodiment, a solvent stream (211) can be fed to the washing column (A22) below the separator stage, where a plurality of separator stages are present below the lowermost separator stage. If a recycled solvent-comprising stream is to be used as the solvent stream (211) instead of fresh solvent, the requirements regarding the maximum isocyanate content are less strict than in the case of stream (210). Owing to the direct contribution of stream (210) to the vapour-liquid equilibrium with the top product stream, in the vapour state, of the washing column, which must be largely isocyanate-free, the isocyanate contents that can be permitted in stream (210) are much lower than in stream (211). Solvent stream (211) can therefore comprise up to 20% by mass isocyanate, based on the total mass of the solvent stream (211).

The use of the condenser in the process according to the invention in step (ii) has the effect, in contrast to the prior art, that the volume stream fed to the washing column (A22) is comparatively small (namely only from 30% to 80% of the corresponding gas stream without step (ii)), comprises considerably less isocyanate (namely preferably from 0% by mass to 5% by mass, particularly preferably from 10 ppm to 0.5% by mass, in each case based on the total mass of stream 206), and a lower temperature (namely preferably from 40° C. to 170° C.). If the condensation temperature in the condenser W23 is suitably chosen (e.g. 60° C.), the volume of the vapour stream to the washing column is reduced by about 55% as compared with the prior art shown in FIG. 1 (207 compared with 106) and reduced by a factor of about 1000 in terms of the amount of isocyanate present.

Consequently, it is possible to work with a washing column of small diameter and with a small number of separator stages in step (iv) according to the invention. The reduced temperature and the associated lower content of quenching liquid in the gas phase passed to the washing column additionally makes necessary a lower power of the condenser of the washing column. The smaller apparatus dimensions mentioned above increase the economy of the process. The cooling capacity displaced from the condenser (W22) of the washing column to the condenser (W23) of step (ii) can be used to obtain steam, preferably low-pressure steam of 6 bar, owing to the higher condensation temperature level.

In comparison with the prior art, less washing liquid has to be used in the washing column (A22) because the vapour stream (207) fed thereto already comprises less isocyanate. According to the prior art, the totality of the washing liquid is conveyed into the quenching zone via the bottom of the washing column and thus determines the solvent content of the liquefied crude product mixture removed at the bottom of the quenching zone. A smaller amount of washing liquid in the process according to the invention thus permits a lower solvent content in the liquid crude product mixture and accordingly a significantly lower outlay in terms of working up in step (vi), without the purification action (that is to say the reduction of the isocyanate content of the gas stream) of step (vi) being reduced compared with the prior art. As a result of the process according to the invention, the amount of circulating solvent and the required electrical pumping capacity are reduced, which is expressed as an energy saving.

In addition to the liquid phase (215), a gaseous stream (214) also forms in step (iv). This gaseous stream consists substantially of hydrogen chloride gas, stoichiometrically excess phosgene, further gases, such as, for example, nitrogen and carbon monoxide, and small amounts of solvent. This gaseous product stream is preferably fed to further working up, where solvent, excess phosgene and resulting hydrogen chloride gas are generally separated from one another. Solvent and excess phosgene (separately from one another) are preferably fed to the reaction again for reasons of economy. The hydrogen chloride can be fed to various possible uses, such as, for example, an oxychlorination of ethylene to ethylene dichloride or a recycling process, which feeds chlorine back into the isocyanate process again. Such recycling processes include the catalytic oxidation of hydrogen chloride, for example according to the Deacon process, the electrolysis of gaseous hydrogen chloride, and the electrolysis of an aqueous solution of hydrogen chloride (hydrochloric acid).

The liquid phase (215) obtained in step (iv) is, if required, conveyed by means of a pump (P22) and in step (v) likewise used as the quenching liquid (216) in step (i). With a suitable apparatus set-up (free liquid run-off is ensured), the pump can be omitted. If required, the stream (215) can be cooled further by means of an additional cooling medium before it is used as quenching liquid (216). The quenching liquid (216) is brought into contact with, preferably injected into, the gaseous product stream (201) preferably at a temperature of from 30° C. to 150° C. Accordingly, in an embodiment, the quenching liquid of step (iii) and the quenching liquid of step (v) are introduced, preferably injected, into the gaseous crude product of the phosgenation (201) separately from one another (209, 216) in step (i). Preferably, the quenching liquid (216) is thereby introduced, preferably injected, into the gaseous crude product stream (201) above the quenching liquid from step (iii) (209). This is because, owing to the fact that, in the process according to the invention, a large part of the isocyanate comprised in the vapours (206) is already separated off in the condenser (W23), the isocyanate content of the liquid phase (215) obtained in step (iv), which is used as quenching liquid (216), falls, as described above. Because isocyanate in the quenching liquid, in particular at the high temperatures in the uppermost part of the quenching zone, leads to increased formation of undesirable secondary products, it is advantageous to feed stream (216) into the quenching zone separately and, relative to the gas stream, upstream of stream (209). As compared with the prior art (FIG. 1), the reduced isocyanate content of (216) in the process according to the invention, as compared with (116), permits an advantageous lower formation of secondary products. However, it is also possible in principle (not shown in FIG. 2) to combine streams (208) and (215) and bring them into contact with, preferably inject them into, the gaseous crude product stream (201) together as a quenching liquid stream. This is preferably effected by passing the condensate stream (208) into the bottom of the washing column (A22), in which the liquid phase (215) is located. A combined quenching liquid stream is then removed from the washing column and used in step (i). The pump (P23) can be omitted in this embodiment.

Step (vi) of the process according to the invention, the working up of the liquid phase (202) obtained in step (i), can be carried out by any process known from the prior art. Partial recycling of the stream (202) to the quenching zone (A21) is not necessary in the process according to the invention; the circulating pump (P11) and the quench cooler (W11), which is potentially susceptible to contamination, can accordingly be omitted. Because the product passes through the quencher only once, it is subjected to thermal stress for a shorter time, which reduces the formation of secondary products. Because the quencher bottom in FIG. 1 at the same time serves as the pump receiver for the large circulating pump (P11), the hold-up of the quencher bottom in the process according to FIG. 2 without a circulating pump or with a substantially smaller product discharge pump can be made smaller, which further reduces the dwell time of the quencher bottom product (202) and accordingly the formation of secondary products. The liquid crude product mixture stream (202) comprises substantially isocyanate, solvent (from the quenching liquid) and a small amount of unreacted phosgene. This liquid crude product mixture stream is then fed to working up by distillation, generally in a plurality of stages, whereby dissolved phosgene and the solvent are separated off. This working up by distillation of the crude isocyanate can be carried out by generally known methods. Examples are described in EP-A-1 413 571, US 2003/0230476 A1 (TDI) and EP 0289 840 B1 (HDI, IDPI and H12-MDI).

The process according to the invention additionally also has the following advantages over the prior art:

Unlike the prior art (FIG. 1), an additional degree of freedom is obtained in the process according to the invention (FIG. 2): As mentioned above, in the process according to the prior art it is necessary when choosing the temperature of the substance streams at the outlet of the quenching zone to balance, on the one hand, low thermal product stress and low solvent and isocyanate content in the vapour stream to be purified and recycled (low temperature is positive) and, on the other hand, low carbamic acid chloride formation and low energy requirement in working up of the product (high temperature is positive). In the process according to the invention, on the other hand, the quencher bottom temperature and the washing column inlet temperature can be chosen independently of one another. The carbamic acid chloride formation is thus reduced and energy is saved in the working up of the product (preheating of the distillation column feed), while at the same time the thermal stress on the product is reduced in terms of time because it passes through the quenching zone only once, and the higher solvent and isocyanate content in the vapour stream does not lead to a larger, more complex washing column.

Figure 2:
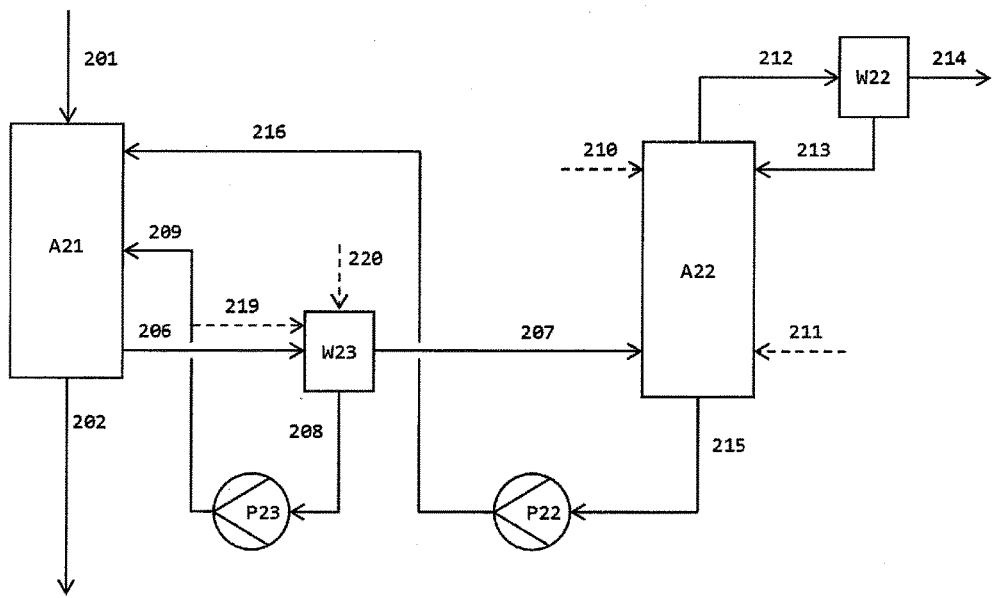
FIG. 2 is a schematic illustration of a preferred form of a process for separating an isocyanate prepared by reaction of a primary amine with an excess of phosgene in the as phase from the gaseous crude product obtained in the reaction, according to the present invention.

At the same quencher bottom temperature, the reduced condensation capacity of the condenser (W22) according to FIG. 2 is "only" "displaced" into the new condenser (W23); however, owing to the higher process-side temperature level in (W23), the apparatus can be constructed smaller and can better be used for a heat-integrative connection of process streams. Owing to the higher process-side temperature level, the cooling capacity can also partially be used for low-pressure steam generation. The same is true for the quencher cooler: The cooling capacity of the quencher cooler (W11), which is omitted, is "only" "displaced" into the new condenser (W23), but, because of the higher heat transfer owing to process-side condensation and the higher temperature change in (W23) on the process side, the apparatus can likewise be made smaller and can better be used for a heat-integrative connection of process streams.

In the process according to FIG. 1, the amount of washing liquid (110) determines the solvent content of the liquid crude product mixture in the quencher bottom (102). A lower solvent concentration reduces the outlay required for working up the product and is therefore advantageous in terms of energy and apparatus. However, the amount of solvent required to achieve sufficient isocyanate washing in the washing column (A12) downwardly limits the desirable reduction of the solvent content in the liquid product mixture (103). This limitation takes effect in particular at low solvent contents in the liquid product mixture (103). In the process according to the invention according to FIG. 2, far lower solvent contents in the liquid crude product mixture are possible because the isocyanate content at the inlet to the washing column is already substantially lower and less washing liquid is therefore required for retaining the isocyanate than according to the prior art (FIG. 1).

In order to keep the quencher bottom temperature constant according to the prior art (FIG. 1), the inlet temperature of the liquid crude product mixture fed back from the quencher bottom to the quencher is conventionally actively controlled. Undesirable variations in the quencher bottom temperature occur in particular in the case of load changes of the reaction zone. In the procedure according to the invention according to FIG. 2, the vapour stream removed from the quencher in vapour form increases as the quencher bottom temperature increases according to the vapour-liquid equilibrium. Accordingly, when the condensation temperature in (W23) is unchanged, there is an automatic increase in the amount of condensate discharged in liquid form, which is fed back as quenching liquid and counteracts the increase in the quencher bottom temperature without active control. Accordingly, the process according to the invention exhibits an advantageous, self-moderating (on account of thermodynamics) dynamic operating behaviour.

EXAMPLES

The processes according to FIG. 1 (comparison Example 1) and FIG. 2 (according to the invention Example 2) were reproduced by means of process simulation. In both cases, at the entry of the reaction zone (not shown in the figures) upstream of (A11) or (A21), the only outlet stream of which is the gaseous crude product stream (101) or (201), there was used a gaseous starting material mixture having the following composition of the major constituents (subordinate amounts of secondary products have been disregarded):

| | |
|---|---|
| Phosgene | 76% by mass |
| TDA isomer | 24% by mass |
| Temperature | 400° C. |
| Pressure | 1400 mbar (abs) |

The volume of the vapour stream to the washing column (207) was 55% smaller in Example 2 than in Example 1

(106), and the washing column in Example 2 (A22) could be configured with a 30% smaller diameter than in Example 1 (A12).

The vapour stream (207) to washing column (A22) comprised an amount of isocyanate that was smaller by a factor of about 1000 than that of the vapour stream (106) to washing column (A12). The amount of washing liquid necessary for operation of washing column (A22), and hence the solvent concentration in the crude product mixture (202), could accordingly be reduced substantially compared with Example 1, without increasing the isocyanate content in the phosgene/hydrogen chloride mixture (214) to be worked up compared with (114).

In the example according to the invention according FIG. 2, the heat exchanger surface (sum of the areas of W23 and W22; as a measure of the apparatus costs) necessary for the process section in question was reduced by 40% compared with Example 1 (FIG. 1, sum of the areas of W11 and W12): although the necessary cooling capacity was comparable in both variants, the condensation operation which took place on the process side in W23 meant that the heat transfer coefficient was greater than in W11, in which a liquid stream is present on the process side. On the coolant side, a liquid coolant was used in all the heat exchangers in question.

In the example according to the invention (FIG. 2), the necessary pump capacity of P23 was only 15% of the corresponding pump P11 according to Example 1 (FIG. 1), which is advantageous inter alia in terms of investment and operating costs.

What is claimed:

1. A process for separating an isocyanate prepared by reaction of a primary amine with an excess of phosgene, comprising:
   (i) converting a gaseous crude product obtained by a gas phase reaction of the primary amine with the excess of phosgene and that comprises at least isocyanate, hydrogen chloride and unreacted phosgene, into a liquid phase comprising at least quenching liquid and isocyanate and a gas phase comprising at least hydrogen chloride and phosgene by contacting the gaseous crude product with at least one quenching liquid;
   (ii) partially condensing the gas phase obtained in step (i) to obtain a condensate and a portion of the gas phase that is not condensed;
   (iii) using the condensate obtained in step (ii) as at least one quenching liquid in step (i);
   (iv) at least partially liquefying the portion of the gas phase not condensed in step (ii) to obtain a liquid phase;
   (v) using the liquid phase obtained in step (iv) as at least one quenching liquid in step (i); and
   (vi) working up the liquid phase obtained in step (i) to pure isocyanate without previously using it as quenching liquid.

2. The process according to claim 1, comprising using a condenser in step (ii) in which the gas phase and the condensate are guided co-currently.

3. The process according to claim 1, wherein the at least partial liquefaction of the portion of the gas phase not condensed in step (ii) is carried out in step (iv) in a washing column having at least one separator stage, wherein at least one solvent stream is fed to the washing column as a washing liquid.

4. The process according to claim 3, comprising removing a gaseous top stream from the washing column and condensing the gaseous top stream in a condenser to obtain a condensate, and feeding the condensate so obtained back into the washing column as additional washing liquid.

5. The process according to claim 3, comprising feeding exactly one solvent stream to the washing column.

6. The process according to claim 3, comprising feeding a solvent stream to the washing column above the separator stage where a single separator stage is present or, where a plurality of separator stages are present, above the uppermost separator stage, wherein the solvent stream comprises isocyanate to be separated off in an amount by mass of from 0 ppm to 100 ppm, based on the total mass of the solvent stream.

7. The process according to claim 3, comprising feeding a solvent stream to the washing column beneath the separator stage where a single separator stage is present or, where a plurality of separator stages are present, beneath the lowermost separator stage, wherein the solvent stream comprises isocyanate to be separated off in an amount by mass of from 0 to 20%, based on the total mass of the solvent stream.

8. The process according to claim 1, comprising obtaining steam by step (ii).

9. The process according to claim 1, comprising bringing the quenching liquid of step (iii) and the quenching liquid of step (v) into contact with the gaseous crude product separately from one another in step (i).

10. The process according to claim 9, comprising bringing the quenching liquid of step (v) into contact with the gaseous crude product above the quenching liquid of step (iii).

11. The process according to claim 1, comprising combining the quenching liquid of step (iii) and the quenching liquid of step (v) and bringing them into contact with the gaseous crude product in step (i) together as a quenching liquid stream.

12. The process according to claim 1, wherein comprising passing:
   (a) a portion of the condensate obtained in step (ii),
   (b) a solvent stream, or
   (c) stream (a) and stream (b)
   into a condenser in addition to the gas phase obtained in step (i).

13. The process according to claim 1, comprising carrying out the contacting of the gaseous crude product with the at least one quenching liquid by injecting the at least one quenching liquid into the gaseous crude product.

14. The process according to claim 1, wherein the primary amine comprises an isomer of toluylenediamnine, an isomer of diphenylmethanediamine, 1,6-hexamethylenediamine, an isomer of isophoronediamine or an isomer of diaminodicyclohexylmethane.

* * * * *